United States Patent [19]

Garro et al.

[11] Patent Number: 4,469,786

[45] Date of Patent: Sep. 4, 1984

[54] DETECTION OF CHEMICAL MUTAGENS IN MARKER RESCUE ASSAY

[75] Inventors: Anthony J. Garro, Tenafly, N.J.; Robert A. Phillips, New York, N.Y.

[73] Assignee: The Mount Sinai School of Medicine of the City University of New York, New York, N.Y.

[21] Appl. No.: 230,037

[22] Filed: Jan. 30, 1981

[51] Int. Cl.$^3$ .................. C12Q 1/70; C12Q 1/68; C12Q 1/02; C12N 15/00
[52] U.S. Cl. .................................... 435/5; 435/6; 435/29; 435/172.1
[58] Field of Search ................... 435/5, 6, 172, 29

[56] References Cited

U.S. PATENT DOCUMENTS 4,332,897 6/1982 Nakano et al. ............... 435/172
4,348,477 9/1982 Nakano et al. ............... 435/172

OTHER PUBLICATIONS

Hayes, *The Genetics of Bacteria and Their Viruses*, Second Edition, John Wiley & Sons Inc., New York, 530–544, (1968).
Scher et al., Journal of Virology, 28(1), 395–402, (1978).
Dubnau et al., J. Bacteriol., 117(2), 488–493, (1974).
Phillips et al., Mut. Res., 74, 267–281, (1980).
Ames et al., Mut. Res., 31, 347–364, (1975).
McCann et al., P.N.AS., 72(3), 979–983, (1975).
Bartsch et al., Cancer Research, 37, 1461–1467, (1977).
Glatt et al., Mut. Res., 67, 113–121, (1979).
Rudner et al., J. Bacteriol., 113(2), 739–753, (1973).
Tevethia et al., J. Bacteriol., 106(3), 802–807, (1971).
Dooley et al., J. Bacteriol., 108(2), 668–679, (1971).
Dubnau et al., J. Mol. Biol., 56, 209–221, (1971).
Rudner et al., Biochim. Biophys. Acta, 149, 199–219, (1967).
Garro, A. J. and Phillips, R. A., Mutation Research, 73, (1980), 1–13.

*Primary Examiner*—Esther M. Kepplinger
*Attorney, Agent, or Firm*—Brumbaugh, Graves, Donohue & Raymond

[57] ABSTRACT

The present application discloses a short-term microbial assay useful in detecting chemical mutagens. A *Bacillus subtilis* which is infected with a strain of the temperate bacteriophage φ105 having a conditional lethal mutation is specifically illustrated. In the assay exogenous DNA from wild-type φ105 is reacted with a potential mutagen and then transfected into the *B. subtilis* carrying a mutated φ105 DNA. After plating, an increase in the frequency of clear plaques signifies that the test compound is mutagenic.

The present invention provides a short-term mutagenicity test which detects frameshift as well as base substitution mutations induced by chemicals.

5 Claims, 7 Drawing Figures

DETECTION OF CHEMICAL MUTAGENS IN MARKER RESCUE ASSAY

The U.S. Government has a paid-up license in this invention and the right in limited circumstances to require the patent owner to license others on reasonable terms as provided for by the terms of contract No. CA22354 awarded by the National Cancer Institute.

Detection of mutagenicity caused by various chemical agents in certain strains of Salmonella is an established procedure as embodied in the well-known Ames test[1]. Furthermore, chemically induced genetic changes in the Ames Salmonella microsome assay are believed to indicate that a particular chemical agent is potentially carcinogenic.
[1]Ames, B. N. et al., *Mutation Res.*, (1975) 31, 347-364.

The Ames test is a reversion assay in which mutated histidine operon genes present in various tester strains are caused to revert to the wild-type after exposure to a chemical mutagen. Detection of mutagenicity in the Ames test requires that the mutagen penetrate the bacterial cell envelope and cause the target gene present in the genome of the test organism to revert without causing cell death. The reversion of the target gene is observed by culturing the treated cells and observing alterations in the growth characteristics of the cells.

However, the Ames assay inherently imposes limitations on the chemicals which can be tested. If the test substance is bactericidal or unable to penetrate the cell envelope, it cannot be assayed by the Ames Salmonella reversion assay. For example, of the 300 chemicals tested by McCann et al.[2] in the Ames Salmonella reversion assay, 10 could not be evaluated because of their toxicity. Lipophilic carcinogens which are not mutagenic in the Ames assay include pesticides and alkyl halides such as dieldrin, DDE, $CCl_4$, and $CHCl_3$[2]; several lipophilic derivatives of the aromatic amine, 2-aminofluorine[3]; and the hormone diethylstilbestrol and several of its metabolites[4].
[2]McCann, J. et al., *Proc. Natl. Acad. Sci.* (US) (1975), 72(3), 979-983.
[3]Bartsch, H. et al., *Cancer Res.* (1977), 37, 1461-1467.
[4]Glatt, H. R., *Mutation Res.* (1979), 67, 113-121.

Another limitation of the Ames test is that it relies on the use of Salmonella strains which carry specific mutations. A positive result is observed when the mutant reverts to its wild form. Such reversion assays are inherently limited by the nature of the mutant. Certain of the mutants which have been used as tester strains specifically detect base substitution mutations; others specifically detect frameshift mutations. For this reason a single strain of Salmonella cannot be relied on to detect both base substitution and frameshift mutagens.

"Frameshift" and "base substitution" mutations are terms used in the field of genetics to characterize the manner in which the DNA molecules have been altered by a mutagen. As is known in the art, DNA, the genetic material of all cells, is polymer containing deoxyribonucleotides. Adenine (A) is always bonded to thymine (T) and guanine (G) is always bonded to cytosine (C). The resultant DNA is usually represented as follows:

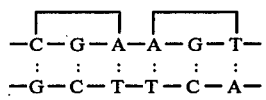

During protein synthesis, the DNA sequence is "read" in triplets (as indicated by the brackets), each triplet coding for a particular amino acid. A frameshift mutation occurs when a nucleotide either is inserted into the sequence or is deleted from the sequence, thereby shifting the normal reading frame for the reading of triplets, and often leading to nonfunctional protein products. A base substitution mutation occurs when a base such as adenine for example is replaced by a guanine, cytosine or thymine. Base substitutions may cause the insertion of a wrong amino acid into a polypeptide chain leading to an inactive protein or may cause chain termination during polypeptide synthesis.

DESCRIPTION OF THE INVENTION

An alternate type of assay depends on the detection of "forward" mutations—i.e., mutagen induced alterations in the wild-type form of a gene. If the phenotype of the mutant produced can readily be detected, mutagenicity, which is a presumptive indication of carcinogenicity, can be assayed irrespective of whether the mutagen caused a frameshift or a base substitution mutation. Moreover, if the DNA which carries the target gene is treated with the test mutagen in vitro, i.e., in an isolated state outside of the cell, and is then transfected into a recipient cell where it will participate in recombination, there is the potential of assaying the mutagenicity of substances which cannot be assayed in cell-based methods because they are unable to penetrate the cell envelope or are toxic to the host cell.

The present invention thus provides a procedure in which isolated DNA is treated with a substance to be assayed. Thereafter the isolated DNA is separated from the substance to be assayed and transfected into the host cell. In this procedure the host cells are never directly exposed to the free form of the test substance. The host cell is then cultured to observe whether mutations were induced. Mutations in the gene selected as the target in the isolated DNA should have a well characterized and easily recognized phenotype upon culturing in a competent host.

The genes which regulate lysogeny in temperate bacteriophages (i.e., viruses which have the potential to replicate either lytically or lysogenically in infected bacteria) should provide suitable target genes for this procedure since either base substitution or frameshift mutations in the genes regulating lysogeny will cause a loss of this mode of replication thereby forcing the mutant bacteriophage to replicate solely in the lytic mode. The manner in which mutations in the genes regulating lysogeny are assayed is explained more fully hereinafter.

Lytic or "virulent" bacteriophages display an extreme form of parasitism, in which the infected bacterial cells are lysed at the end of the bacteriophage growth cycle. In contrast to the virulent bacteriophages "temperate" bacteriophages have, in addition to the capacity for lytic replication, the ability to replicate lysogenically, a mode of replication which is characterized by the persistence of the bacteriophage DNA in the bacterial cells for many cell generations. In most cases the DNA of the lysogenic bacteriophage becomes incorporated into the DNA of the host bacterium as a "prophage", and is thus replicated in the host bacterial cells through successive generations. Under suitable conditions, the repressed prophage can be activated and induced to multiply lyptically, thereby killing the host cells which liberate newly formed bacteriophage particles as they lyse.

Virulent and temperate bacteriophages are assayed by the plaque method, wherein a bacteriophage-containing sample is mixed with susceptible bacteria in a soft agar and poured over the surface of petri dish containing a layer of hard nutrient agar which has been previously set. The virus particles diffuse through the soft agar until each infects a bacterium in which it multiplies. The virulent bacteriophages cause the bacteria to lyse, releasing progeny virus. These, in turn, infect neighboring bacteria, which again lyse and release more progeny. Meanwhile, the uninfected bacteria multiply to form a dense, opaque area of growth (usually referred to as a "lawn"). After a period of incubation, the areas of lyse cells stand out as a clear transparent plaque against the lawn.

When a susceptible bacterial strain is infected by a temperate bacteriophage, two alternative responses are displayed. Some bacterial cells are lysed while others are lysogenized. Because temperate bacteriophages lyse only a fraction of the cells that they infect, and because the lysogenized cells are immune to superinfection, the plaques produced are turbid. Mutants which have lost the ability to lysogenize produce clear rather than turbid plaques.

In the present invention the occurrence of mutations in the genes controlling lysogeny is detected by the so-called "marker rescue" technique. The production of clear plaque mutants generated by exposure of the isolated DNA of a temperate bacteriophage to mutagenic chemicals should, in theory, be assayable by simple transfection, a process in which isolated bacteriophage DNA is introduced into cells which are competent for the uptake of exogenous DNA. The production of clear plaque forming bacteriophage by transfection requires, however, that all the genes essential for bacteriophage replication survive exposure to the test agent. Since the genes controlling lysogeny comprise only a small percentage of the bacteriophage genome, the target size ratio of genes regulating lysogeny to genes essential to replication is unfavorable.

The target size problem can be circumvented by using a marker rescue assay. In the marker rescue assay the competent host cells not only are transfected with the mutagen-treated DNA but also are infected with a bacteriophage containing a conditional lethal mutation in a gene which is tightly linked to the genes regulating lysogeny and which is required for plaque formation on a non-supressing (Sup$^-$) host (i.e., a host which lacks the gene product that can reverse the phenotypic effect of the conditional lethal mutation). The infecting lethally mutated bacteriophage provides an intact genome, which in the host cell undergoes recombination with the mutagen-treated DNA. Since the mutagen-treated DNA carries the wild-type allele of the essential gene which is mutated in the infecting bacteriophage, the recombination events between the transfecting and infecting DNAs generate "rescued" bacteriophage capable of plaquing on Sup$^-$ cells. If the transfecting DNA is also carrying a mutagen-induced lesion in any of the lysogeny-controlling genes, that are linked to the rescued essential gene, then clear plaque mutants are produced. This process is diagrammatically depicted in FIG. 7.

The advantage of a marker rescue based assay over a transfection-based assay is that in marker rescue plaque formation with the mutagen-treated DNA requires only that the wild-type allele ($Ess_1^+$) corresponding to the gene carrying the conditional lethal mutation ($Ess_1^-$) survive the exposure to the mutagenic agent. Since there are multiple closely linked genes which control lysogeny, there is a favorable target size ratio with respect to mutagenic events, which result in formation of clear plaquing phage, versus inactivating events which block plaque formation.

Thus, in summary, the invention broadly contemplates a procedure for assaying the potential mutagenicity of an agent, which procedure comprises: (1) isolating DNA containing the wild-type genome of a temperate bacteriophage and thereafter transfecting said DNA into competent cells, wherein (a) said cells have been infected with a conditional lethal mutant of the temperate bacteriophage which will infect said cells, the conditional lethal mutant bacteriophage being characterized by (i) a wild-type immunity region which regulates lysogeny, and (ii) genes essential for replication of the bacteriophage, one of which is closely linked to the immunity region and which closely linked gene is in a mutated form, which mutation blocks the multiplication of the infecting bacteriophage within said cells; and (b) said isolated bacteriophage DNA is a wild-type DNA homologous to the DNA of the bacteriophage with which said cells were infected, said wild-type DNA, preferably dispersed in a solvent, having been brought into reactive relation with said substance to be assayed for potential mutagenicity, thereafter separated therefrom, and transfected into said cells; and (2) assaying the transfected/infected cells for the production of clear plaquing mutant bacteriophage.

The preferred form of the invention utilizes a mutant of temperate *Bacillus subtilis* bacteriophage known as $\phi 105^5$. The mutant carries a conditional lethal mutation which blocks plaque formation by $\phi 105$ in cells which are non-suppressing. A conditional lethal mutant known as Jsus11 is one such mutated bacteriophage. Bacteriophage capable of plaquing on non-suppressing cells are generated by recombination (rescue) between DNA molecules originally joined to the Jsus11 allele and wild-type J+ allele which is linked to the genes regulating lysogeny.

[5] Scher, B. M. et al., *J. Virol.* (1978) 28, 395–402.

The J gene is tightly linked to a cluster of about six genes referred to as the immunity region whose functions are required for lysogeny. A chemically induced mutation which inactivates any of the immunity region genes results in the production of a clear plaquing phage which is readily distinguishable from the turbid plaquing wild-type phage.

BACTERIAL AND BACTERIOPHAGE STRAINS

The bacterial strains which can be used as the host for marker rescue in carrying out this invention are characterized by being (1) competent with respect to the uptake of exogenous phage DNA which has been treated with the putative mutagen and (2) non-permissiveness with respect to replication of the conditionally lethal mutant infecting phage which participates in the marker rescue reaction. Representative *Bacillus subtilis* strains, which can be used in this invention, and their genotypes are listed in Table 1.

TABLE 1

| Bacterial Strains | | |
|---|---|---|
| Strain | Synonym | Genetic Markers |
| GB68 | BD99 | hisA trpC2 thr-5 |
| GB7075 | JBO1-200 | hcr-9 trpC2 |

Strain GB68 is preferably grown to a relatively high level of competence for the uptake of exogenous DNA by the method of Dubnau[6] and is the preferred host for the marker rescue experiments. However, Strain GB7075 can also be used as the host even though it is defective for excission repair.

[6]Dubnau, D. and Cirigliano, C., *J. Bacteriol.*, (1974), 117, 488-493.

The bacteriophages used must be infectious for the host bacteria and have (1) a wild-type phenotype which is temperate and (2) a related conditional lethal mutation, in which the mutant gene is closely linked to the immunity region, that can be transfected into the host for purposes of the marker rescue assay. Wild-type $\phi 105$ and the conditional lethal mutant $\phi 105$Jsus11 are suitable for use in this invention when *B. subtilis* is the host cell. The bacteriophage 100 105 has been deposited under strain number 1P12 with the Bacillus Genetic Stock Center at The Ohio State University, Columbus, Ohio 43210. $\phi 105$Jsus11 can be obtained by induction of the *B. subtilis* strain GB1115, deposited as strain No. 1L19. The clear-plaque deletion mutant of $\phi 105$ known as DII:6C can be used as a substitute for wild-type $\phi 105$ as a source of DNA to be treated with potentially mutagenic agents in tests designed to detect the ability of potential mutagens to disrupt linkage between the J gene and the immunity region. A representative $\phi 105$DII:6C has been deposited as strain No. 1P13.

MEDIA AND GROWTH OF PHAGE AND BACTERIA

Plaques are assayed by standard overlay procedure. A typical medium for $\phi 105$ which may be used for this purpose is: 1% tryptone broth, 0.5% NaCl, 10 mM MgSO$_4$, and 0.2% maltose. The bottom agar can be solidified with 1-2% agar while the corresponding top agar contains about 0.6% agar.

In assaying for the production of clear plaque mutants it is desirable to block the growth in the overlays of the marker rescue recipient cells because some of these cells may have been lysogenized and such cells may block plaque formation. Blockage of this growth may be accomplished by incorporating an antibiotic to which the marker rescue recipient cells are susceptible in the plaque assay plates and using antibiotic-resistant cells, which are susceptible to the rescued bacteriophage released by the marker rescue recipient cells. Streptomycin has been used for this purpose at a concentration of around 1 mg/ml.

$\phi 105$Jsus11 phage can be prepared by induction of GB1115 (deposited with The Genetic Stock Center as strain No. 1L19) by addition of mitomycin C, at a concentration of about 0.4 $\mu$g/ml, to exponentially growing cells in medium consisting of 2.5% veal infusion plus 0.5% yeast extract in distilled water (hereinafter "VY broth"). The frequency of spontaneous J+ revertants which are present in each preparation of determined by plaque assay on the permissive GB43, and non-permissive GB17, cell lines of *B. subtilis* and is generally $<10^{-7}$. GB43 and GB17 have been deposited as strains Nos. 1A14 and 1A461, respectively.

Host cells can be made competent for uptake of DNA by the methods described by Rudner and Remeza (1973)[7], Tevithia and Mandel (1971)[8] or Dooley et al. (1971)[9]. We have used the method of Rudner et al.[7] The cells are stored frozen until use at $-80°$ C. in medium containing 10% glycerol[10].

[7]Rudner, R., *J. Bacteriol.* (1973), 113, 739-753.
[8]Tevithia, M. and Mandel, M., *J. Bacteriology* (1971) 106, 802-807.
[9]Dooley, D. C. et al., *J. Bacteriology* (1971) 108, 668-679.
[10]Phillips, A. et al., *Mutation Res.* (1980) 74, 267-281.

DNA ISOLATION

Wild-type $\phi 105$ DNA is preferably used in its replicative form since this form is more active in both transfection and marker rescue than the mature form of the DNA. Such DNA can be prepared from suitable infected host cells. For example, GB68 can be grown in VY broth containing 0.01M NaCl to a density of about $5 \times 10^7$ CFU/ml. The cells may be pelleted by centrifugation and infected with $\phi 105$ at a multiplicity of infection of 2 to 3 by resuspending the cells in a bacteriophage lysate for 20 min. The infected cells are typically diluted into fresh, warmed VY broth and incubated with shaking at 37° C. for 30 min. The infected cells then are concentrated by centrifugation and lysed enzymatically (i.e., lysozyme). The nucleic acids can be separated from proteins by pronase and phenol extraction of the lysate as described by Dubnau and Davidoff-Abelson[11]. The nucleic acid-containing aqueous phase is collected, precipitated (for instance by 2 volumes of ethanol) and following removal of the phenol by dialysis, the RNA is digested (for instance with a mixture of enzymes such as pancreatic and TI RNases), and the phenol extraction is repeated. The isolated DNA can be stored at 4° C. at a concentration of about 400-600 $\mu$g/ml.

[11]Dubnau, D. and Davidoff-Abelson, R., *J. Mol. Biol.* (1971), 56, 209-221.

MARKER RESCUE

The frozen competent host cells such as GB68 or GB7075 (deposited under strain numbers 1A242 and 1A455, respectively with the Bacillus Genetic Stock Center) are thawed and diluted in a transformation medium, for instance Rudner et al[12]. Aliquots of cells, i.e. 0.5 ml, were infected with $\phi 105$Jsus11 bacteriophage at a multiplicity of 3 to 5 and the mixture was incubated at 37° C. for 15 min. The infected cells are preferably pelleted by centrifugation and resuspended either in 0.5 ml of the same transformation medium, if the test DNA has not been denatured, or in the case of denatured DNA, in 0.5 ml of a modified medium optionized for transformation with single-stranded DNA. DNA is added to the transformation medium to obtain a final concentration of 4 $\mu$g/ml and the cells are incubated with shaking at 37° C. for 30 min. The cells then are repelleted and resuspended in 2 ml VY broth and incubated with shaking at 37° C. for 4 hours, which is sufficient for 3 to 4 cycles of bacteriophage replication. The lysates are diluted and assayed for $\phi 105$ wild-type and $\phi 105$ clear-plaque seeded with GB17. The overlay plates are scored after overnight incubation at 37° C.

[12]Rudner, R. et al., *Biochem. Biophys. Acta* (1967), 149, 199-219.

The data from the mutagenesis experiment can be presented as the frequency of clear plaque forming units (PFU)/total PFU observed per sample. In general, with the control DNA samples in each experiment there are no clear plaques observable among <100,000 PFU scored and thus the background frequency of clear PFU/total PFU is described as $<10^{-5}$.

DNA-MUTAGEN REACTIONS

The capacity of this invention to detect chemical mutagens was assessed by a series of well characterized DNA-reactive mutagens. The compounds were selected on the basis of their producing different lesions in DNA and included the following: hydroxylamine (HA), which induces predominantly guanine-cytosine to adenine-thymine transitions by its effect on cytosines; N-methyl-N'-nitro-N-nitrosoguanidine (MNNG), a compound whose mutagenic potency has been related to its capacity to alkylate oxygens in nucleic acids; chloroacetaldehyde (CAA), a vinyl chloride metabolite which reacts with adenines and cytosines to form imidazonucleoside derivatives; propylene oxide (PO), an aliphatic epoxide which reacts with guanine and adenine residues but has also been claimed to react with the phosphodiester backbone of DNA producing strand scissions; and N-acetyl-N-acetoxy-2-aminofluorene (AAAF), a potent frameshift mutagen which forms two different guanine adducts, N-(deoxyguanosin-8-yl)-AAF and 3-(deoxyguanosin-$N^2$-yl)-AAF.

In carrying out the mutagenesis reactions all of the test chemicals, with the exception of HA, were reacted with the DNA (100 μg/ml) in a solvent consisting of a 1:1 (v/v) solution of dimethylformamide (DMF) and solution of 0.15M and 0.015M sodium citrate (SSC/10). There are two advantages of the DMF solvent: (1) it lowers the melting temperature of the DNA from 72.5° C. (in SSC/10) to 36° C. thus allowing the DNA bases to be in an exposed, more chemically reactive state at relatively low temperatures and (2) it solubilizes many poorly water soluble chemicals.

The HA reactions were conducted in a sodium phosphate buffer of pH 6.2 at a temperate of 53° C.

Following reaction with the test chemicals the DNA was recovered by ethanol precipitation, in the presence of 80 μg of carrier t-RNA, and was dissolved in SSC/10 at a DNA concentration of 20 μg/ml. The incubation of the bacteriophage DNA in the DMF or phosphate buffers in the absence of added mutagen did not increase the spontaneous frequency of clear plaque mutants observed following marker rescue.

Our new microbial assay is illustrated further in the following examples and figures in which.

EXAMPLE 1

Following the procedures described above, double-stranded DNA of φ105, strain number 1P12 was isolated and incubated with 1M HA. The reaction mixture, containing 100 μg/ml DNA, 1M HA in 0.1M sodium phosphate buffer of pH 6.2, was incubated at 53° C. Samples of the mixture were taken after 0, 10, 20, 40 and 60 minutes and the mutagen treated DNA was isolated, and used for marker rescue using competent GB68 as the recipient. the competent GB68 had been previously infected with φ105 Jsus11 as described above.

Figure 1:
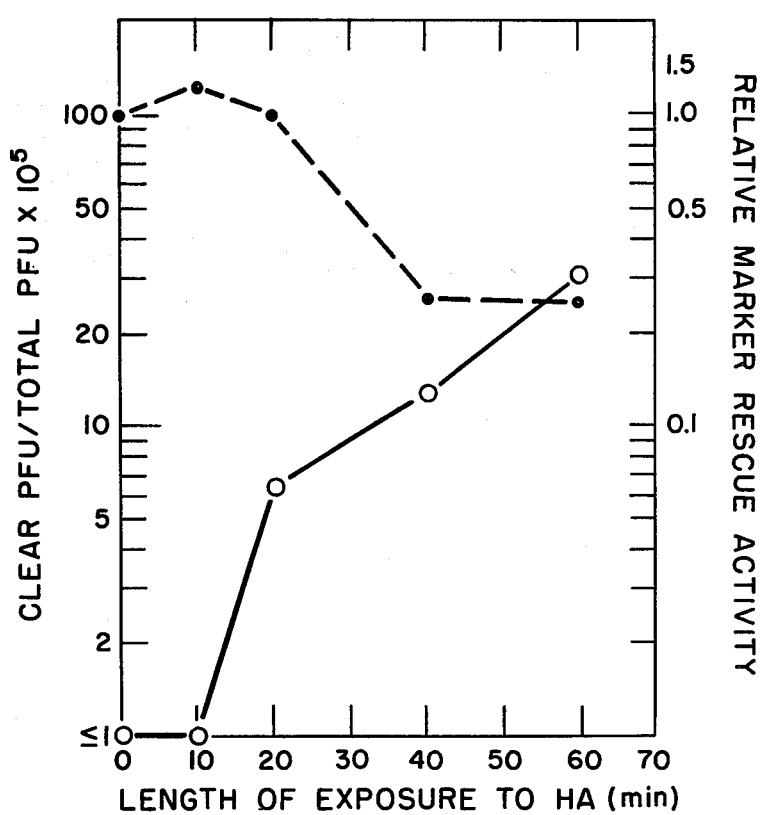
FIG. 1 is a graph showing HA induced mutagenesis of double-stranded φ105 DNA.

The results are summarized in FIG. 1 by the frequency of clear PFU/total PFU (solid line) and relative marker rescue activity (broken line). A time dependent increase in the capacity of the treated DNAs to generate clear-plaque mutants was found.

EXAMPLE 2

The procedure described in Example 1 was repeated except single-stranded DNA was incubated at 45° C.

Figure 2:
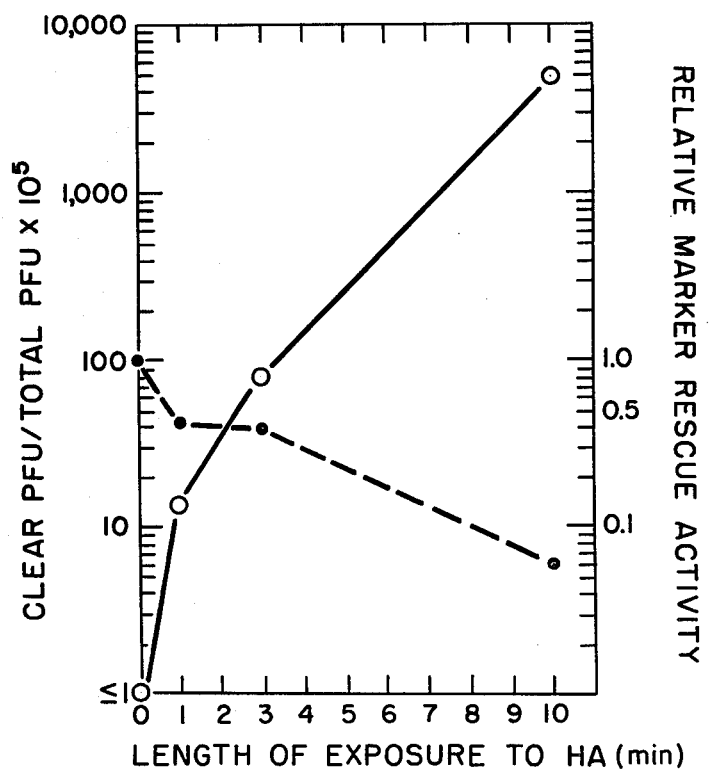
FIG. 2 is a graph showing HA induced mutagenesis of single-stranded φ105 DNA.

The results are summarized in FIG. 2 by the frequency of clear PFU/total PFU (solid line) and relative marker rescue activity (broken line). A time dependent increase in the capacity of the treated DNA to generate clear-plaque mutants is shown. Mutagenesis occurred more rapidly and more mutants were generated with DNA which has been denatured prior to exposure to HA relative to undenatured DNA which was seen in FIG. 1. Incubation with HA also resulted in a loss of marker rescue activity. This loss of activity occurred more rapidly with single-stranded DNA during the mutagenesis test.

EXAMPLE 3

The procedure described in Example 1 was repeated except the reaction mixture contained 100 μg/ml single-stranded φ105 DNA and 100 mM MNNG in the DMF buffer of pH 6.1. Samples of the MNNG mixture were taken after an incubation at 42° C. for 0, 2.5, 5 and 10 minutes.

Figure 3:
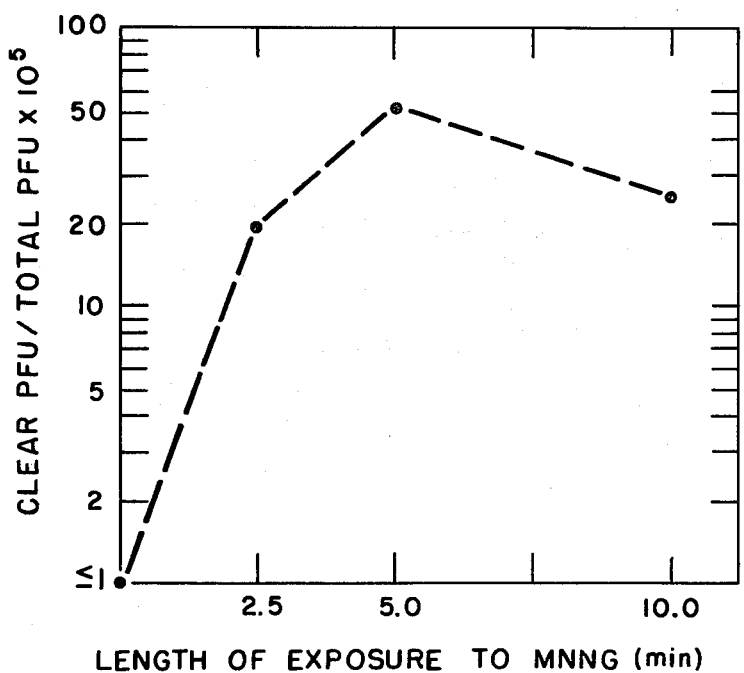
FIG. 3 is a graph showing MNNG induced mutagenesis of single-stranded φ105 DNA.

The results are summarized in FIG. 3 by the frequency of clear PFU/total PFU (broken line). Mutations were induced under these conditions with the increase in frequency of clear PFU being significant at a $p<0.001$. There was no significant decrease in marker rescue activity over the time course of the experiment.

EXAMPLE 4

The procedure described in Example 3 was repeated except the reaction mixtures contained 1 to 4 mM of CAA. The reaction mixtures were incubated at 50° C. for 15 minutes. The DNA samples were tested for their ability to generate clear-plaque mutants with GB68 and with the host cell reactivation (Hcr$^-$) mutant, GB7075, which is defective in excission repair of damaged DNA.

Figure 4:
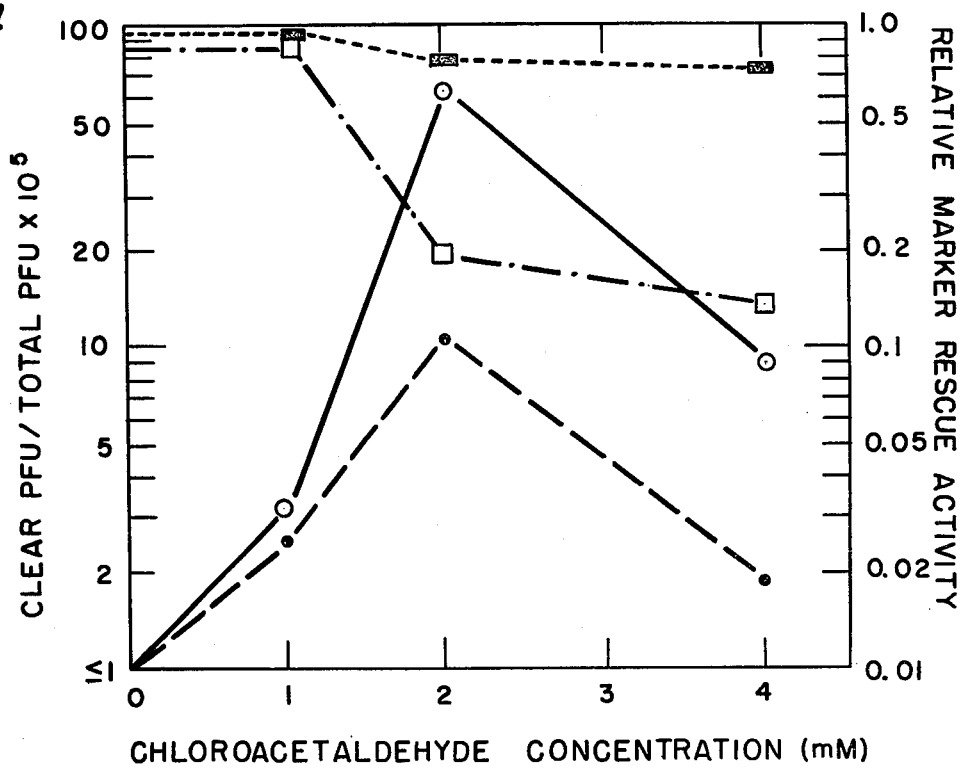
FIG. 4 is a graph showing CAA induced mutagenesis of single-stranded φ105 DNA.

The results of the experiment are presented in FIG. 4 which shows the frequency of clear PFU/total PFU with GB68 (broken line) or GB7075 (solid line) and relative marker rescue activity with GB68 (broken line with bars) or GB7075 (dot dash line). The method of this invention was found to effectively assay the occurrence of mutants using either GB68 or GB7075 as the host bacteria but with the repair-defective Hcr$^-$ host GB7075 being more sensitive than the Hcr$^+$ host with respect to detection of the CAA-induced mutants. The inactivation of marker rescue activity also was more pronounced in the Hcr$^-$ strain. With both the Hcr$^-$ and Hcr$^+$ strains as recipients the increase in the frequency of clear PFU is significant at $p<0.001$.

EXAMPLE 5

The marker rescue assay is dependent upon the incorporation of linked genes for the detection of mutagenic activity. An agent which reacts with the DNA backbone may produce strand scissions which disrupt the gene linkages. Since PO reacts with the DNA bases as well as with the DNA backbone, PO was tested to determine whether disruption of linkage is observable by marker rescue.

Figure 5:
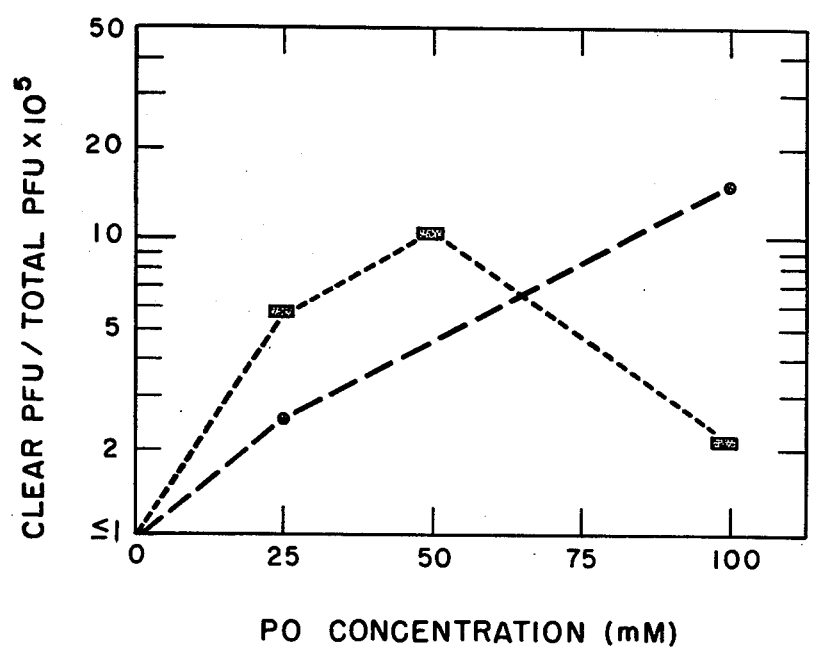
FIG. 5 is a graph showing PO induced mutagenesis of single-stranded φ105 DNA.

The procedure described in Example 3 was repeated except the reaction mixtures contained 25 to 100 mM of PO. The presence of mutagenic lesions in the treated DNA sample was detected by marker rescue with the Hcr$^+$ and Hcr$^-$ recipient strains, GB68 and GB7075 respectively. The results of the experiment are shown in FIG. 5 using GB68 (broken line with squares) and GB7075 Hcr-9 (broken line with circles). The increase in the frequency of clear PFU was significant with both strains at a $p<0.001$. No consistent decrease in marker rescue activity was observed although there was a decrease in the frequency of clear PFU generated with the Hcr+ host at the highest PO concentration.

EXAMPLE 6

In order to directly measure the effect of PO on gene linkage in the marker rescue assay, replicative-form $\phi$105DII:6C DNA was treated with PO under the same conditions as described in Example 5. $\phi$105DII:6C DNA carries a deletion mutation which produces a clear-plaque phenotype and thus generates a high frequency of clear-plaquing phage when used to rescue Jsus11. PO-induced strand scissions between the J+ allele and the DII:6C mutation should decrease the frequency of clear PFU resulting from Jsus11 rescue. The experiment demonstrated that there was no significant disruption of linkage as assayed by marker rescue. This result is in contrast to the PO-induced strand scission which was observed in a transformation-based mutagenesis assay described by Phillips et al.[10]. This finding indicates that the linkage between the immunity region genes and Jsus11 is relatively resistant to the effects mutagens which are known to cause DNA strand scissions.

[10]Phillips, A. et al., *Mutation Res.* (1980) 74, 267–281.

EXAMPLE 7

Figure 6:
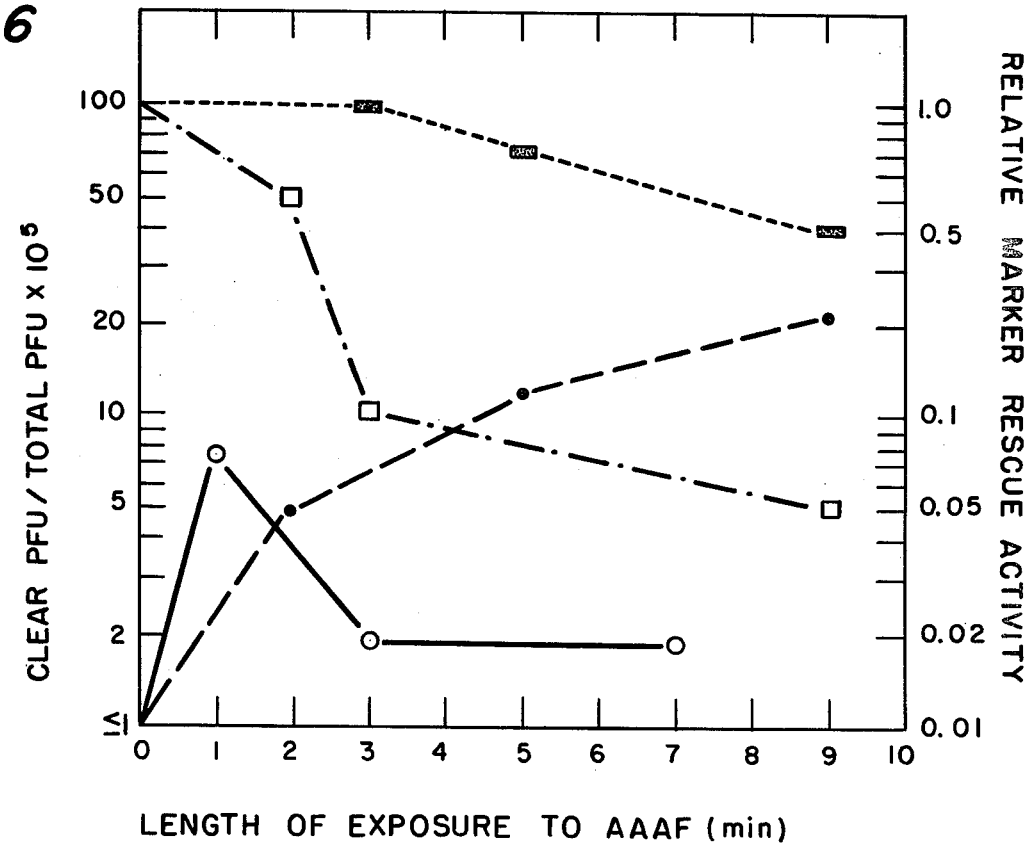
FIG. 6 is a graph showing AAAF induced mutagenesis of single-stranded φ105 DNA.
Figure 7:
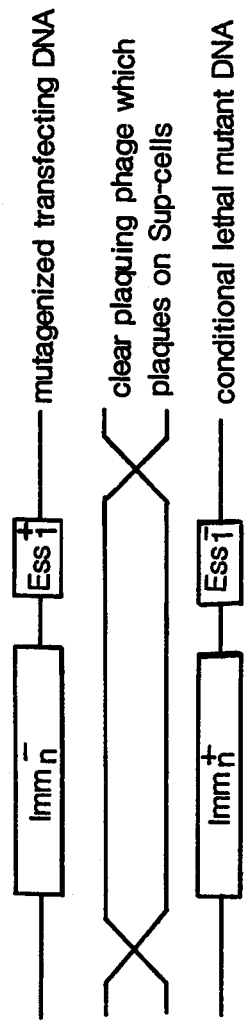
FIG. 7 is a diagram of a recombination cross.

The procedure described in Example 3 was repeated except the reaction mixture contained 35 mM of AAAF. After incubation at 37° C. for 1-9 min., the DNA samples were assayed in both the Hcr+ and Hcr− strains, GB68 and GB7075 respectively, for the production of clear-plaque mutants. The results obtained are presented in FIG. 6 by the frequency of clear PFU/total PFU with Gb68 (broken line) or GB7075 (solid line) and relative marker rescue with GB68 (square broken line) or GB7075 (dot dash line).

The numbers of clear-plaque mutants generated by the treated DNA with the repair-proficient Hcr+ recipient increased with length of AAAF treatment. With the Hcr− recipient, however, while there appeared to be an increase in the frequency of clear PFU generated with the earliest sample tested there also was a very rapid and extensive loss of marker rescue activity in subsequent samples and a concomitant decrease in the frequency of clear-plaque mutants observed. The increase in the frequency of clear PFU was significant with a $p<0.001$ with the Hcr+ strain and with a $p<0.025$ with the Hcr− strain.

We claim:

1. A method for assaying, a substance for potential mutagenicity, which method comprises:
   (1) isolating DNA containing the wild-type genome of a temperate bacteriophage to obtain an isolated bacteriophage DNA and thereafter transfecting said DNA into competent cells, wherein
   (a) said cells have been infected with conditional lethal mutant of the temperate bacteriophage which will infect said cells, the conditional lethal mutant bacteriophage being characterized by (i) a wild-type immunity region which regulates lysogeny and (ii) genes essential for replication of the bacteriophage, one of which is closely linked to the immunity region and which closely linked gene is in a mutated form which blocks the multiplication of the infecting bacteriophage within said cells; and
   (b) said isolated bacteriophage DNA is a wild-type DNA homologous to the DNA of the bacteriophage with which said cells were infected, said wild-type DNA having been brought into reactive relation with said substance to be assayed for potential mutagenicity, thereafter separated therefrom, and transfected into said cells;
   (2) assaying the transfected/infected cells for the production of clear plaquing mutant bacteriophage.

2. The method of claim 1, wherein said competent cells are bacteria of the species *Bacillus subtilis*.

3. The method of claim 2, wherein said bacteria are *Bacillus subtilis* deposited under strain numbers 1A242 or 1A455 with the Bacillus Genetic Stock Center.

4. The method of claim 1, wherein said bacteriophage is *Bacillus subtilis* $\phi$105 deposited under strain number 1P12 with the Bacillus Genetic Stock Center.

5. The method of claim 1, wherein in step (1)(b) the wild-type DNA is dispersed in dimethylformamide, in an amount effective to lower the melting temperature of the DNA, to increase the reaction between the DNA and the substance to be tested.

* * * * *